(12) United States Patent
Metten et al.

(10) Patent No.: US 8,328,882 B2
(45) Date of Patent: Dec. 11, 2012

(54) GENTLE DYEING AND LIGHTENING AGENTS HAVING IMPROVED LIGHTENING POWER

(75) Inventors: Diane Metten, Duesseldorf (DE); Ina Franke, Duesseldorf (DE); Gabriele Weser, Neuss (DE); Juergen Schoepgens, Schwalmtal (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/421,939

(22) Filed: Mar. 16, 2012

(65) Prior Publication Data

US 2012/0171135 A1     Jul. 5, 2012

Related U.S. Application Data

(63) Continuation of application No. PCT/EP2010/060705, filed on Jul. 23, 2010.

(30) Foreign Application Priority Data

Sep. 17, 2009  (DE) .......................... 10 2009 029 548

(51) Int. Cl.
*A61Q 5/10* (2006.01)
(52) U.S. Cl. ............. 8/405; 8/406; 8/431; 8/435; 8/597; 8/604

(58) Field of Classification Search .............. 8/405, 406, 8/431, 435, 597, 604
See application file for complete search history.

(56) References Cited

U.S. PATENT DOCUMENTS 6,423,101 B1 *  7/2002  Yaker et al. ....................... 8/405
2010/0297049 A1   11/2010  Samain et al.

FOREIGN PATENT DOCUMENTS

WO      2009080670 A2      7/2009

* cited by examiner

*Primary Examiner* — Eisa Elhilo
(74) *Attorney, Agent, or Firm* — David LeCroy

(57) ABSTRACT

Cosmetics for oxidatively dyeing and/or lightening keratin fibers, especially human hair, containing, in a cosmetic carrier, at least one oxidant chosen from hydrogen peroxide and/or the solid addition products thereof attaching to inorganic or organic compounds, at least one alkanolamine of formula (I), $NH_{3-x}(CH_2CH_2OH)_x$(I), where x is one of the numbers 1, 2, or 3, and at least one alkanolamine of formula (II), where R1 and R2 are independently hydrogen, a $C_1$-$C_6$ alkyl group, or a $C_1$-$C_6$ hydroxyalkyl group or R1 and R2 form a ring along with the carbon atom of the alkano-lamine, said ring having 4 to 8 ring atoms and optionally containing 1 to 2 heteroatoms, provided that R1 and R2 do not simultaneously represent hydrogen, wherein the cosmetic is ammonia-free.

12 Claims, No Drawings

GENTLE DYEING AND LIGHTENING AGENTS HAVING IMPROVED LIGHTENING POWER

CROSS REFERENCE TO RELATED APPLICATIONS

The present application is a continuation of International Patent Application No. PCT/EP2010/060705 filed 23 Jul. 2010, which claims priority to German Patent Application No. 10 2009 029 548.8 filed 17 Sep. 2009, both of which are incorporated herein by reference.

The present invention relates to agents for oxidative lightening and/or dyeing of keratinic fibers, particularly human hair, comprising at least two structurally different alkanolamines and at least one oxidizing agent, wherein the agents are free of ammonia, as well as their use for improving grey coverage and improving lightening power.

Modifying the shape and color of hair represents an important area of modern cosmetics. Consumers resort to lightening or color-changing agents for fashionable hair style color schemes or for concealing grey or even white hair with fashionable or natural color tints. In addition to the desired coloration and lightening power, these agents should induce as little damage as possible to the hair and preserve the fiber structure.

For the provision of color-changing cosmetic agents, especially for keratin-containing fibers such as human hair, the person skilled in the art is aware of diverse dyeing systems based on dyeing requirements. For permanent, intensive dyeing with corresponding fastness, oxidation dyes are used in which the actual dyes are formed from oxidation dye precursors under the influence of oxidizing agents or atmospheric oxygen. Oxidation dyes are characterized by excellent, long lasting coloration results. For temporary colorations, colorants or toners having substantive dyes as the coloring component are usually used. These are dye molecules that are directly absorbed onto the substrate and do not require any oxidative process to develop the color.

Preparations of oxidizing agents such as a solution of hydrogen peroxide are usually used for lightening or blonding human hair. This lightening can be combined with oxidative coloration operations or colorations with substantive dyes.

In spite of their advantageous coloration properties, oxidative lightening and hair dyeing agents present disadvantages for the user. Prior to their application on human hair, oxidative dyes are usually blended with dilute aqueous solutions of hydrogen peroxide. This mixture is then applied to the hair and rinsed out again after a defined contact time. Use of these oxidizing agents for coloring or developing the actual coloration leads to damage in hair structure and the hair surface. An improvement in the coloration power of an agent with respect to color intensity would permit a reduction in the application amount or application time.

Furthermore, oxidative dyeing and lightening processes on keratinic fibers usually proceed under alkaline pH, especially from 9.0 to 10.5. Such pH values are required in order to ensure that the external squamosal layer (cuticula) opens, thereby enabling the active species (dye precursors and/or hydrogen peroxide) to penetrate into the hair. The alkalizing agent used is typically ammonia; ammonia, however, is disadvantageous for the user because of its intensive smell and possible irritation, including irritations of the skin and sensitization of the skin.

Even if the lightening and dyeing agents that have been available on the market up to now generally have good dyeing powers, as a result of their high concentrations of oxidizing and alkalizing agents and due to their potential skin irritation they cannot be considered as optimal.

Accordingly, the present invention is directed towards improving fastness properties, grey coverage power and lightening power of colorations of ammonia-free hair dyes/hair lighteners to such an extent that they are comparable with or superior to customary ammonia-containing agents available on the market, and at the same time, however, exhibit reduced damage to the hair.

It has now been found in an unpredictable manner that a significant improvement in the lightening power can be achieved on keratinic fibers by adding certain alkanolamines as the alkalizing agent instead of ammonia in color-modifying, oxidative agents. Oxidative hair dyes also display an improved lightening power with this alkalization.

The person skilled in the art has been aware for some time of the addition of monoethanolamine or 2-amino-2-methylpropanol in the hair coloration. Until now it has not been considered in the prior art that with the specific combination of two alkanolamines, the agent can be used at the same pH in ammonia-free colorants and still retain excellent lightening and dyeing powers.

Accordingly, a first subject matter of the present invention is an agent for oxidatively dyeing and/or lightening of keratinic fibers, especially human hair, comprising in a cosmetic carrier at least one oxidizing agent chosen from hydrogen peroxide and/or its solid addition products on inorganic or organic compounds,
at least one alkanolamine according to Formula (I), $$NH_{3-x}(CH_2CH_2OH))_x \qquad (I),$$

wherein x is one of the numbers 1, 2 or 3, and
at least one alkanolamine according to Formula (II),

(II)

wherein R1 and R2 each independently represent hydrogen, a $C_1$-$C_6$ alkyl group or a $C_1$-$C_6$ hydroxyalkyl group or R1 and R2 together with the carbon atom of the alkanolamine form a ring that possesses 4 to 8 ring atoms and optionally can comprise 1 to 2 hetero atoms, with the proviso that R1 and R2 do not simultaneously stand for hydrogen,
wherein the agent is free of ammonia.

Keratinic fibers or keratin fibers are understood to mean furs, wool, feathers and particularly human hair. Although agents according to the invention are primarily suitable for dyeing keratin fibers, in principle nothing prevents their use in other fields.

Preparations used for the inventive use comprise the active substances in a cosmetic carrier. In the context of the invention, this cosmetic carrier is aqueous, alcoholic or aqueous-alcoholic. For the purposes of the present invention, aqueous-alcoholic carriers refer to water-containing solutions comprising 3 to 70% by weight of a $C_1$-$C_4$ alcohol, particularly ethanol or isopropanol, based on total weight of the application mixture. Agents according to the invention can additionally comprise further organic solvents such as 4-methoxybutanol, ethyl diglycol, 1,2-propylene glycol, n-propanol, n-butanol, n-butylene glycol, glycerin, diethylene glycol monoethyl ether, and diethylene glycol mono-n-butyl ether. Preference is given here to all water-soluble organic solvents. In the context of the invention, an aqueous carrier comprises at least 30 wt %, especially at least 50 wt % water, based on total weight of the application mixture. For the purposes of dyeing the hair, such carriers include creams, emulsions, gels or surfactant-containing foaming solutions such as shampoos, foam aerosols or other preparations suitable for use on the hair. Emulsions and gels represent preferred carriers, wherein emulsions are particularly preferred.

In the context of the invention, the terms "free of ammonia" or "poor in ammonia" and "ammonia-free" refer to the amount of ammonia added to the agent, wherein the added ammonia can be added both as an aqueous, alcoholic, aqueous-alcoholic or other solution, as well as by injection of gaseous ammonia or by adding liquefied ammonia. However, the ammonia can also be added by using appropriate ammonium salts, wherein the ammonium cation, depending on the pH of the preparation, is in equilibrium with its corresponding base, the ammonia itself. Accordingly, in the context of the invention, the terms "ammonia-free" or "poor in ammonia" also refer to agents that comprise ammonium salts.

The term "free of ammonia" means that the ready-for-use agent comprises less than 2 wt % added ammonia, based on total weight of the ready-for-use preparation. Should ammonium salts be present in the ready-for-use agent, then the ammonia content that results from these salts, assuming a total deprotonation of the ammonium cations, is correspondingly less than 2 wt %, based on total weight of the ready-for-use preparation. Preferred poor in ammonia agents comprise less than 1 wt %, especially less than 0.5 wt % and quite particularly preferably less than 0.1 wt % of added ammonia, based on total weight of the ready-for-use preparation. Ammonia-free in the context of the invention are those agents to which no ammonia has been added by one of the above described methods. Such agents are inventively particularly preferred.

As the first essential ingredient, the preparation according to the invention comprises at least one alkanolamine according to Formula (I), $NH_{3-x}(CH_2CH_2OH)_x$ (I), wherein x is one of the numbers 1, 2 or 3. Inventively suitable alkanolamines of Formula (I) are monoethanolamine (2-aminoethanol; (x=1)), diethanolamine (bis-(2-hydroxyethyl)amine; (x=2)) and triethanolamine (tris-(2-hydroxyethyl)amine; (x=3)). Particularly preferred agents comprise monoethanolamine as the alkanolamine according to Formula (I).

In one embodiment of the present invention, the agents comprise 0.5 to 15 wt % of an alkanolamine according to Formula (I), preferably 1 to 10 wt % and particularly preferably 2 to 6 wt %, based on the ready-for-use agent.

As a further essential ingredient, the inventive preparation comprises at least one alkanolamine according to Formula (II)

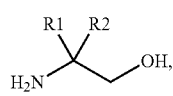

(II)

wherein R1 and R2 are independently hydrogen, a $C_1$-$C_6$ alkyl group or a $C_1$-$C_6$ hydroxyalkyl group or R1 and R2 together with the carbon atom of the alkanolamine form a ring that possesses 4 to 8 ring atoms and optionally can comprise 1 to 2 hetero atoms, with the proviso that R1 and R2 are not simultaneously hydrogen.

Exemplary $C_1$-$C_6$ alkyl groups are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$.

Exemplary $C_1$-$C_6$ hydroxyalkyl groups are —$CH_2OH$, —$CH_2CH_2OH$, —$CH_2CH_2CH_2OH$, —$CH_2CH(OH)CH_3$ and —$CH_2CH_2CH_2CH_2OH$, the —$CH_2CH_2OH$ group being preferred.

Exemplary compounds wherein R1 and R2 together with the carbon atom of the alkanolamine form a ring having 4 to 8 ring atoms and can optionally comprise 1 to 2 hetero atoms are 1-amino-1-hydroxymethylcyclooctane, 1-amino-1-hydroxymethylcycloheptane, 1-amino-1-hydroxymethylcyclohexane, 1-amino-1-hydroxymethylcyclopentane, 1-amino-1-hydroxymethylcyclobutane, 4-amino-4-hydroxymethylpiperidine, 3-amino-3-hydroxymethylpiperidine, 4-amino-4-hydroxymethyltetrahydropyran, 3-amino-3-hydroxymethyltetrahydropyran, 3-amino-3-hydroxymethylpyrrolidine, 3-amino-3-hydroxymethyltetrahydrofuran.

One embodiment is wherein the agent comprises as the alkanolamine according to Formula (II) at least one compound according to Formula (II), wherein R1 and/or R2 stand for a $C_1$-$C_6$ alkyl group, or R1 and R2 together with the carbon atom of the alkanolamine stand for a cyclopentyl group, a cyclohexyl group or a tetrahydropyran group.

Particularly preferably, R1 and R2 each stand for a methyl group.

In one embodiment of the present invention, the agents comprise 0.5 to 15 wt % of an alkanolamine according to Formula (II), preferably 1 to 10 wt % and particularly preferably 2 to 6 wt %, based on the ready-for-use agent.

A preferred embodiment of the present invention is wherein the inventive agent comprises the alkanolamine according to Formula (I) and at least one compound according to Formula (II) as the alkanolamine according to Formula (II), wherein R1 and R2 each stand for a methyl group.

Preferred agents comprise alkanolamines according to Formula (I) and alkanolamines according to Formula (II) in a total amount of 0.5 to 25 wt %, preferably 1 to 20 wt % and particularly preferably 4 to 12 wt %, based on total weight of the ready-for-use agent, wherein the weight ratio between alkanolamines according to Formula (I) and alkanolamines according to Formula (II) is a value from 1 to 10 to 10 to 1, preferably 1 to 2 to 2 to 1.

Preferred agents comprise equal weight fractions of alkanolamines according to Formula (I) and alkanolamines according to Formula (II).

As a third essential ingredient, the agent comprises as the oxidizing agent an oxidizing agent chosen from hydrogen peroxide and its addition products on solid inorganic or organic compounds.

Preferably, hydrogen peroxide itself is used as an aqueous solution. However, hydrogen peroxide can also be added in the form of a solid addition compound of hydrogen peroxide onto inorganic or organic compounds, such as sodium perborate, sodium percarbonate, magnesium percarbonate, sodium percarbamide, polyvinyl pyrrolidone $nH_2O_2$ (n is a positive integer greater than 0), urea peroxide and melamine peroxide. In the last named case the addition compounds release hydrogen peroxide in the inventive application mixture. These agents comprise free hydrogen peroxide in addition to the addition compound in the cosmetic carrier.

The hydrogen peroxide is inventively quite particularly preferably metered as an aqueous hydrogen peroxide solution to the inventive agent. The concentration of a hydrogen peroxide solution is firstly determined from the statutory regulations and secondly according to the required effect; preferably 6 to 25 wt % solutions in water are used. Inventively preferred agents comprise, based on their total weight, 0.01 to 25 wt %, preferably 0.1 to 15 wt %, particularly preferably 1 to 12 wt % of hydrogen peroxide (calculated as 100% $H_2O_2$).

In a preferred embodiment, lightening and dyeing agents according to the invention comprise at least one color changing component. The color changing component is chosen from at least one oxidation dye precursor and/or substantive dyes and/or nature-analogous dyes.

In an embodiment of the present invention, the agent comprises at least one oxidation dye precursor and/or substantive dye as the color changing component. In a preferred embodiment, the dyeing preparation comprises at least one oxidation dye precursor as the color changing component.

Dyeing preparations comprise at least one developer component and optionally at least one coupler component as the oxidation dye precursor. Developer components can develop the actual dyes from themselves but preferably with coupler components. Therefore, dyes according to the invention preferably contain at least one oxidation dye precursor of the developer type and at least one oxidation dye precursor of the coupler type. Developer and coupler components are usually employed in free form. For substances with amino groups, it can, however, be preferred to employ them in salt form, especially in the form of hydrochlorides and hydrobromides or sulfates.

Here, developer components and coupler components are generally used in approximately molar amounts relative to one another. Although molar use has proven to be expedient, a certain excess of individual oxidation dye precursors is not disadvantageous, such that developer components and coupler components can be present in a molar ratio of 1:0.5 to 1:2.

Suitable oxidation dye precursors of the developer type are p-phenylenediamine and its derivatives. Preferred p-phenylenediamines are chosen from one or more compounds of p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis-(2-hydroxyethyl)-p-phenylenediamine, 4-N,N-bis-(2-hydroxyethyl)-amino-2-methylaniline, 4-N,N-bis-(2-hydroxyethyl)-amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2, 3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane as well as their physiologically acceptable salts. Inventively particularly preferred p-phenylenediamine derivatives are chosen from at least one compound of the group p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine as well as the physiologically acceptable salts of these compounds.

According to the invention, it may also be preferred to use compounds as the developer component which have at least two aromatic nuclei that are substituted by amino and/or hydroxyl groups. Preferred binuclear developer components are especially chosen from at least one compound of N,N'-bis-(2-hydroxyethyl)-N,N'-bis-(4'-aminophenyl)-1,3-diamino-2-propanol, N,N'-bis-(2-hydroxyethyl)-N,N'-bis-(4'-aminophenyl)ethylenediamine, N,N'-bis-(4'-aminophenyl) tetramethylenediamine, N,N'-bis-(2-hydroxy-ethyl)-N,N'-bis-(4'-aminophenyl)-tetramethylenediamine, N,N'-bis-(4-(methylamino)phenyl)tetra-methylenediamine, N,N'-diethyl-N,N'-bis-(4'-amino-3'-methylphenyl) ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine and 1,10-bis-(2',5'-diaminophenyl)-1,4, 7,10-tetraoxadecane as well as their physiologically acceptable salts. Particularly preferred binuclear developer components are chosen from among N,N'-bis-(2-hydroxyethyl)-N,N'-bis-(4-aminophenyl)-1,3-diamino-2-propanol, bis-(2-hydroxy-5-aminophenyl)methane, 1,3-bis-(2,5-diaminophenoxy)-2-propanol, N,N'-bis(4-aminophenyl)-1,4-diazacycloheptane, 1,10-bis-(2,5-diaminophenyl)-1,4,7,10-tetraoxadecane or one of their physiologically acceptable salts.

Moreover, it may be inventively preferred to use a p-aminophenol derivative or one of its physiologically acceptable salts as the developer component. Preferred p-aminophenols are p-aminophenol, N-methyl-p-aminophenol, 4-amino-3-methyl-phenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol as well as their physiologically acceptable salts. p-Aminophenol, 4-amino-3-methylphenol, 4-amino-2-aminomethylphenol, 4-amino-2-(1,2-dihydroxyethyl)phenol and 4-amino-2-(diethylaminomethyl)phenol are particularly preferred compounds.

Furthermore, the developer component can be chosen from o-aminophenol and its derivatives, such as 2-amino-4-methylphenol, 2-amino-5-methylphenol or 2-amino-4-chlorophenol.

In addition, the developer component can be chosen from heterocyclic developer components, such as from pyrimidine derivatives, pyrazole derivatives, pyrazolopyrimidine derivatives and their physiologically compatible salts. Preferred pyrimidine derivatives include the compounds 2,4,5,6-tetraaminopyrimidine, 4-hydroxy-2,5,6-triaminopyrimidine, 2-hydroxy-4,5,6-triaminopyrimidine, 2-dimethylamino-4,5, 6-triaminopyrimidine, 2,4-dihydroxy-5,6-diaminopyrimidine and 2,5,6-triaminopyrimidine. Preferred pyrazole derivatives are the compounds that are selected from 4,5-diamino-1-methylpyrazole, 4,5-diamino-1-(2-hydroxyethyl) pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl) pyrazole, 4, 5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino- 3-methyl-1-isopropylpyrazole, 4-amino-5-(2-aminoethyl)amino-1,3-dimethylpyrazole, as well as their physiologically acceptable salts, especially 4,5-diamino-1-(2-hydroxyethyl)pyrazole. Pyrazolo[1,5-a]pyrimidines are particularly preferred as the pyrazolopyrimidines, wherein preferred pyrazolo[1,5-a]pyrimidines are chosen from pyrazolo[1,5-a]pyrimidine-3,7-diamine, 2,5-dimethyl-pyrazolo[1,5-a]pyrimidine-3,7-diamine, pyrazolo[1,5-a]pyrimidine-3,5-diamine, 2,7-dimethylpyrazolo[1,5-a]pyrimidin-3,5-diamine, 3-amino-pyrazolo[1,5-a]pyrimidin-7-ol, 3-aminopyrazolo[1,5-a]pyrimidin-5-ol, 2-(3-aminopyrazolo[1,5-a]-pyrimidin-7-ylamino)ethanol, 2-(7-aminopyrazolo[1,5-a]pyrimidin-3-ylamino)ethanol, 2-[(3-amino-pyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine as well as their physiologically acceptable salts and their tautomeric forms.

Particularly preferred developer components are chosen from at least one compound from p-phenylenediamine, p-toluylenediamine, 2-(2-hydroxy-ethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-2-propanol, bis-(2-hydroxy-5-aminophenyl)methane, 1,3-bis-(2,5-diaminophenoxy)-2-propan-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxy-ethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, as well as the physiologically acceptable salts of these compounds. Quite particularly preferred developer components are p-toluylenediamine, 2-(2-hydroxyethyl)-p-phenylenediamine, 2-methoxy-methyl-p-phenylenediamine, N-(4-amino-3-methylphenyl)-N-[3-(1H-imidazol-1-yl)propyl]amine, and/or 4,5-diamino-1-(2-hydroxyethyl)pyrazole as well as their physiologically acceptable salts. The developer components are preferably used in an amount of 0.0001 to 10 wt %, preferably 0.001 to 5 wt %, based on the ready-for-use agent.

Coupler components alone, in the context of the oxidative dyeing, do not form any significant coloration; rather, they always need the presence of developer components. Therefore it is inventively preferred that when using at least one coupler component, at least one developer component is also used. Coupler components according to the invention are preferably chosen from m-aminophenol and/or its derivatives, m-diaminobenzene and/or its derivatives, o-diaminobenzene and/or its derivatives, o-aminophenol and/or its derivatives, naphthaline derivatives with at least one hydroxyl group, di- or trihydroxybenzene and/or its derivatives, pyridine derivatives, pyrimidine derivatives, monohydroxyindole derivatives and/or monoaminoindole derivatives, monohydroxyindoline derivatives and/or monoaminoindoline derivatives, pyrazolone derivatives such as 1-phenyl-3-methylpyrazol-5-one, morpholine derivatives such as 6-hydroxybenzomorpholine or 6-aminobenzomorpholine, quinoxaline derivatives such as 6-methyl-1,2,3,4-tetra-hydroquinoxaline, and/or mixtures of two or more compounds from one or more of these classes.

The inventively useable m-aminophenols or their derivatives are preferably chosen from at least one compound of 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol and their physiologically acceptable salts.

The inventively useable 3-diaminobenzenes or their derivatives are preferably chosen from at least one compound of m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxy-ethoxy)-5-methylphenylamine, 1-amino-3-bis-(2'-hydroxyethyl)aminobenzene and their physiologically acceptable salts.

The inventively useable o-diaminobenzenes or their derivatives are preferably chosen from at least one compound from 3,4-diaminobenzoic acid and 2,3-diamino-1-methylbenzene and their physiologically acceptable salts.

Preferred di- or trihydroxybenzenes and their derivatives are chosen from at least one compound from resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

The inventively useable pyridine derivatives are preferably chosen from at least one compound from 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and their physiologically acceptable salts.

Preferred naphthalene derivatives with at least one hydroxyl group are chosen from at least one compound from 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

The inventively useable indole derivatives are preferably chosen from 4-hydroxyindole, 6-hydroxyindole and 7-hydroxyindole and their physiologically acceptable salts.

The inventively useable indoline derivatives are preferably chosen from 4-hydroxyindoline, 6-hydroxyindoline and 7-hydroxyindoline and their physiologically acceptable salts.

Preferred pyrimidine derivatives are chosen from at least one compound from 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and their physiologically acceptable salts.

According to the invention, particularly preferred coupler components are chosen from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)-ethanol, 1,3-bis(2,4-diaminophenoxy)propane, 1-methoxy-2-amino-4-(2-hydroxyethylamino)-benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or their physiologically acceptable salts. In this regard, resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine and 1-naphthol as well as their physiologically acceptable salts are particularly preferred. The coupler components are preferably used in an amount of 0.0001 to 10 wt %, preferably 0.001 to 5 wt %, based on the ready-for-use agent.

The agents for the inventive use can further comprise at least one substantive dye. These are dyes that are directly absorbed onto the hair and do not require any oxidative process to develop the color. Substantive dyes are usually nitrophenylenediamines, nitroaminophenols, azo dyes, anthraquinones or indophenols. Substantive dyes can be classified into anionic, cationic and non-ionic substantive dyes. The substantive dyes are preferably employed in quantities of 0.001 to 20 wt %, particularly 0.05 to 5 wt %, based on total end-use preparation. The total amount of substantive dyes is preferably a maximum of 20 wt %.

Preferred anionic substantive dyestuffs are known compounds with the designations Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromophenol blue.

Preferred cationic substantive dyes are cationic triphenylmethane dyes such as Basic Blue 7, Basic Blue 26, Basic Violet 2 and Basic Violet 14, aromatic systems substituted with a quaternary nitrogen group, such as Yellow 57, Basic Red 76, Basic Blue 99, Basic Brown 16 and Basic Brown 17 and HC Blue 16, as well as Basic Yellow 87, Basic Orange 31 and Basic Red 51.

Non-ionic nitro and quinone dyes and neutral azo dyes are particularly suitable as non-ionic substantive dyes. Preferred non-ionic substantive dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

It is not required that each of the optionally comprised substantive dyestuffs be pure compounds. In fact, due to manufacturing processes for the individual dyes, minor quantities of even more components may be present as long as they have no detrimental influence on the coloration result or that they must be excluded on other grounds (e.g., toxicological).

In addition, naturally occurring dyestuffs may also be added such as are found, for example, in henna red, henna neutral, henna black, chamomile leaves, sandalwood, black tea, alder buckthorn bark, sage, logwood, madder root, cachou, cedar and alkanet root.

Dyestuff precursors of nature-analogous dyes that are used are preferably those indoles and indolines having at least one hydroxyl and/or amino group, preferably as the substituent on the six-membered ring. These groups can carry further substituents (e.g., in the form of an etherified or esterified hydroxyl group or an alkylated amino group). In another embodiment, the colorants comprise at least one indole and/or indoline derivative. Preparations according to the invention having precursors of nature-analogous dyes are preferably used as the atmospherically oxidative colorant. In this embodiment, an additional oxidizing agent is consequently not added to the cited compositions. Dye precursors of nature-analogous dyes are each preferably employed in an amount of 0.001 to 5 wt %, based on total end-use preparation.

Derivatives of 5,6-dihydroxyindoline, particularly 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline and/or 5,6-dihydroxyindoline-2-carboxylic acid, particularly preferably 5,6-dihydroxyindoline, are particularly suitable as the precursors of nature-analogous hair dyes. Derivatives of 5,6-dihydroxyindole, particularly 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole and/or 5,6-dihydroxyindole-2-carboxylic acid, particularly preferably 5,6-dihydroxyindole, are also eminently suitable as the precursors of nature-analogous hair dyes.

Taking into account the previously cited preferred embodiments, a special and explicitly preferred embodiment is illustrated when the agent for dyeing keratinic fibers is free of ammonia and comprises in a cosmetic carrier a combination of monoethanolamine and 2-amino-2-methylpropanol as well as additionally at least one oxidation dyestuff product chosen from p-toluylendiamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole together with their physiologically acceptable salts, and, as the third component, hydrogen peroxide in the already described preferred weight fractions.

Finally, quite particularly preferred agents are free of ammonia and have the following combination, wherein the weight contents again refer to total weight of the ready-for-use agent:

2.0 to 6.0 wt % monoethanolamine,
2.0 to 6.0 wt % 2-amino-2-methylpropanol
and 3.0 to 12.0 wt % hydrogen peroxide.

Finally, in addition, agents are quite particularly preferred that are free of ammonia and have the following combination, wherein the weight contents again refer to total weight of the ready-for-use agent:

2.0 to 6.0 wt % monoethanolamine,
2.0 to 6.0 wt % 2-amino-2-methylpropanol,
0.1 to 5.0 wt % of oxidation dye precursors
and 3.0 to 12.0 wt % hydrogen peroxide.

In the course of the investigations of this invention, it was shown that the addition of certain fatty compounds can produce a further improvement in the lightening power and the grey covering capability.

In this regard, preferred fatty compounds are chosen from fatty alcohols, fatty acid esters with mono and polyhydroxylated alcohols as well as esters of fatty alcohols with short chain mono and dicarboxylic acids with $C_2$-$C_6$ parent substances.

Here, particularly preferred fatty compounds are the fatty acid esters of fatty alcohols, wherein the fatty acid and fatty alcohol can be saturated or unsaturated and preferably have 8 to 30, more preferably 8 to 22 carbon atoms in the chain.

In one embodiment of the present invention, the agent additionally comprises at least one fatty component chosen from fatty acid alkyl esters of the formula $RCO_2R'$, wherein R is a $C_7$-$C_{21}$ alkyl group or $C_7$-$C_{21}$ alkenyl group and R' is a $C_8$-$C_{22}$ alkyl group or $C_8$-$C_{22}$ alkenyl group.

Inventively preferred fatty acid alkyl esters are chosen from decyl laurate, decyl myristate, decyl palmitate, decyl stearate, decyl oleate, lauryl laurate, lauryl myristate, lauryl palmitate, lauryl stearate, lauryl oleate, myristyl laurate, myristyl myristate, myristyl palmitate, myristyl stearate, myristyl oleate, cetyl laurate, cetyl myristate, cetyl palmitate, cetyl stearate, cetyl oleate, stearyl laurate, stearyl myristate, stearyl palmitate, stearyl stearate, stearyl oleate, oleyl laurate, oleyl myristate, oleyl palmitate, oleyl stearate, oleyl oleate as well as mixtures thereof. Agents according to the invention preferably additionally comprise decyl oleate (trade name, e.g., Cetiol V, Saboderm) and/or oleyl oleate (trade name, e.g., Cetiol, Edenor ODO).

In an embodiment of the present invention, the agents comprise fatty acid alkyl esters of the formula $RCO_2R'$ in a total weight of 0.5 to 10 wt %, preferably 1 to 5 wt %, based on total weight of the agent according to the invention.

According to the invention, an oxidation dyeing composition or an oxidative lightener can also be applied to the hair together with a catalyst that activates oxidation of the dye precursors (e.g., by atmospheric oxygen). Such catalysts include certain enzymes, iodides, quinones or metal ions.

In addition, it has proven advantageous when the dyes and/or lighteners comprise at least one stabilizer or complexant. Common and in the context of the present invention, preferred chelating complexants include polycarboxylic acids, nitrogen-containing mono or polycarboxylic acids, especially ethylenediaminetetraacetic acid (EDTA), ethylenediaminedisuccinic acid (EDDS) and nitrilotriacetic acid (NTA), geminal diphosphonic acids, in particular 1-hydroxyethane-1,1-diphosphonic acid (HEDP), amino phosphonic acids such as ethylenediaminetetra(methylenephosphonic acid) (EDTMP), diethylenetriaminepenta(methylenephosphonic acid) (DTPMP), phosphonopolycarboxyic acids such as 2-phosphonobutane-1,2,4-tricarboxylic acid as well as cyclodextrins, alkali metal stannates (sodium stannate), alkali metal pyrophosphates (tetrasodium pyrophosphate, disodium pyrophosphate), alkali metal phosphates (sodium phosphate), and phosphoric acid. According to the invention the agents preferably comprise 0.01 to 3 wt %, more preferably 0.05 to 1 wt % complexant, based on total weight of the agent according to the invention.

In an application of additional oxidizing agents, the actual lightening or dyeing preparation is advantageously produced immediately prior to application by mixing an inventive preparation comprising at least one combination of at least one alkanolamine according to Formula (I) and at least one alkanolamine according to Formula (II), as well as a preparation comprising the oxidizing agent chosen from hydrogen peroxide and/or its sold addition product on inorganic or organic compounds.

Inventively useable agents can additionally comprise blonding and/or bleaching agents and thus be made available as agents that dye and lighten at the same time. In the following, agents of this type will be called "dyes", "lightening dyes" or "dyes and tighteners". Employing only hydrogen peroxide or its addition products on organic or inorganic compounds is often insufficient however, for strongly lightening very dark hair.

Consequently, should the consumer feel the need for very strong blonding, in another embodiment it can be inventively preferred for the dye to additionally comprise at least one inorganic persulfate salt or peroxydisulfate salt in the agent for lightening the keratinic fibers. Preferred peroxydisulfate salts are ammonium peroxydisulfate, potassium peroxydisulfate and sodium peroxydisulfate. The ready-for-use agent can preferably comprise the peroxydisulfate salts in an amount of 0.1 to 25 wt %, particularly in an amount of 0.5 to 15 wt %, based on total weight of the ready-to-use agent.

Inventively useable agents are preferably formulated as free-flowing preparations. These include especially emulsions, suspensions and gels, particularly preferably emulsions. The free-flowing preparations preferably additionally comprise an emulsifier or surfactant as the surface active substance, wherein surface active substances are designated as surfactants or emulsifiers depending on their field of application, and are chosen from anionic, cationic, zwitterionic, amphoteric and non-ionic surfactants.

Suitable anionic surfactants for the inventive preparations include all anionic surface-active materials suitable for use on the human body. Preferred anionic surfactants are linear and branched fatty acids containing 8 to 30 carbon atoms (soaps), alkyl sulfates, alkyl ether sulfates and polyethoxylated ether carboxylic acids containing 10 to 18 carbon atoms in the alkyl group and up to 12 glycol ether groups in the molecule.

Zwitterionic surfactants are those surface-active compounds having at least one quaternary ammonium group and at least one carboxylate, sulfonate or sulfate group in the molecule. Betaines are particularly suitable zwitterionic surfactants. A preferred zwitterionic surfactant is the fatty acid amide derivative known under the INCI name Cocamidopropyl Betaine.

In another embodiment, the agent additionally comprises at least one amphoteric surfactant. Examples of suitable ampholytic surfactants are N-alkylglycines, N-alkylamino propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids. Particularly preferred amphoteric surfactants are marketed under the INCI name Disodium Cocoamphodipropionate and Disodium Cocoamphodiacetate.

Alkyl polyglycosides, particularly $C_8$-$C_{22}$ alkyl mono- and alkyl oligo-glycosides and their ethoxylated analogs, are suitable non-ionic surfactants. Alkylene oxide addition products on saturated, linear fatty alcohols and fatty acids, each with 2 to 30 moles ethylene oxide per mole fatty alcohol or fatty acid, have proved to be additional preferred non-ionic surfactants. Preparations with excellent properties are also obtained when they comprise fatty acid esters of ethoxylated glycerin as the non-ionic surfactant.

According to the invention, cationic surfactants of the type quaternary ammonium compounds, the esterquats and the amido amines are likewise preferred. Preferred quaternary ammonium compounds are ammonium halides, such as alkyltrimethylammonium chlorides, dialkyldimethylammonium chlorides and trialkylmethylammonium chlorides, as well as the imidazolium compounds known under the INCI names Quaternium-27 and Quaternium-83. Quaternized protein hydrolysates are further inventively useable cationic surfactants. The alkylamido amines are normally manufactured by amidation of natural or synthetic fatty acids and fatty acid fractions with dialkylamino amines (e.g., Tegoamid® S 18 (stearamidopropyldimethylamine)). Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines.

The anionic, non-ionic, zwitterionic or amphoteric surfactants are present in amounts of 0.1 to 45 wt %, preferably 1 to 30 wt % and particularly preferably 1 to 15 wt %, based on total amount of the ready-for-use agent. The compositions used according to the invention preferably comprise cationic surfactants in amounts of 0.05 to 10 wt %, particularly preferably 0.1 to 5 wt %, based on total composition.

Furthermore, agents according to the invention can have additional active substances, auxiliaries and additives, such as cationic polymers, non-ionic polymers (vinyl pyrrolidinone/vinyl acrylate copolymers, polyvinyl pyrrolidinone, vinyl pyrrolidinone/vinyl acetate copolymers, polyethylene glycols and polysiloxanes); zwitterionic and amphoteric polymers (acrylamidopropyl-trimethyl-ammonium chloride/acrylate copolymers and octylacrylamide/methyl methacrylate/tert-butylaminoethyl methacrylate/2-hydroxypropyl methacrylate copolymers); anionic polymers (polyacrylic acids, crosslinked polyacrylic acids, vinyl acetate/crotonic acid copolymers, vinyl pyrrolidinone/vinyl acrylate copolymers, vinyl acetate/butyl maleate/isobornyl acrylate copolymers, methyl vinyl ether/maleic anhydride copolymers and acrylic acid/ethyl acrylate/n-tert-butylacrylamide terpolymers); thickeners (agar-agar, guar-gum, alginates, xanthan gum, gum arabicum, karaya gum, locust bean flour, linseed gums, dextrans, cellulose derivatives (e.g., methyl cellulose, hydroxyalkyl cellulose and carboxymethyl cellulose), starch fractions and derivatives such as amylose, amylopectin and dextrins, clays such as bentonite or fully synthetic hydrocolloids such as polyvinyl alcohol; hair conditioning compounds (phospholipids, for example, soja lecithin, egg lecithin, cephalines as well as silicon oils); protein hydrolysates of vegetal or animal origin (elastin-, collagen-, keratin-, milk protein-, soja protein- and wheat protein hydrolysates, their condensation products with fatty acids as well as quaternized protein hydrolysates); perfume oils, dimethyl isosorbit and cyclodextrins; fiber structure improving substances (mono-, di- and oligosaccharides, glucose, maleic acid and lactic acid); defoamers such as silicones (dimethicon); dyes for coloring the agent; anti-dandruff active substances (piroctone olamine, zinc omadine and climbazol); light-protective agents (derivatized benzophenones, cinnamic acid derivatives and triazines); active substances (pantolactone, allantoin, pyrrolidinone carboxylic acids and their salts as well as bisabolol); vitamins, provitamins and vitamin precursors, particularly those of the groups A, $B_3$, $B_5$, $B_6$, C, E, F and H; vegetal extracts; vegetal oils (macadamia nut oil, candle nut oil, palm oil, amaranth seed oil, peach stone oil, avocado oil, olive oil, cocoa oil, rape seed oil, sesame oil, jojoba oil, soja oil, peanut oil, evening primrose oil and tea tree oil); cholesterol; texturizers (sugar esters, polyol esters or polyol alkyl ethers); fats and waxes (fatty alcohols, beeswax, montan wax and paraffins); swelling and penetration substances (glycerin, propylene glycol monoethyl ether, carbonates, hydrogen carbonates, guanidines, ureas such as primary, secondary and tertiary phosphates); opacifiers (latex, styrene/PVP copolymers and styrene/acrylamide copolymers); pearlizers (ethylene glycol mono and distearate as well as PEG-3-distearate); blowing agents such as propane-butane mixtures, $N_2O$, dimethyl ether, $CO_2$ and air; antioxidants.

The person skilled in the art selects these additional materials as a function of the desired properties of the preparations. The inventive preparations preferably comprise the additional active substances, auxiliaries and additives in amounts of 0.01 to 25 wt %, especially 0.05 to 15 wt %, based on total amount of the ready-for-use agent.

The dye preparations of the inventive use preferably exhibit a pH in the range 4 to 12. For oxidation dyes, application of the dye occurs in a weakly alkaline medium, preferably at a pH of 8.0 to 10.5. In the context of the present invention, pH values refer to those measured at a temperature of 22° C.

For adjusting the pH, the person skilled in the art is aware of commonly used acidifying and alkalization agents, besides the ammonia that must be avoided if possible and the inventive combination of the structurally different alkanolamines. Alkalization agents that can be used for adjusting the pH are typically chosen from inorganic salts, especially of the alkali metal and alkaline earth metals, organic alkalization agents, especially amines and basic amino acids. Inventively preferred acidifiers are food acids such as citric acid, acetic acid, malic acid or tartaric acid, as well as diluted mineral acids. Inventively useable inorganic alkalization agents are preferably chosen from sodium hydroxide, potassium hydroxide, calcium hydroxide, barium hydroxide, sodium phosphate, potassium phosphate, sodium silicate, potassium silicate, sodium carbonate and potassium carbonate. Sodium hydroxide and/or potassium hydroxide are particularly preferred. The basic amino acids are preferably chosen from L-arginine, D-arginine, D/L-arginine, L-lysine, D-lysine, D/L-lysine, particularly preferably L-arginine, D-arginine and D/L-arginine. The additional acidifiers and alkalizers are each preferably present in amounts of 0.05 to 15 wt %, particularly 0.5 to 10 wt %, based on total weight of the ready-for-use agent.

The ready-for-use dyeing and/or lightening agent is applied onto the keratinic fibers and left on the fibers, particularly in the hair, for a specified contact time. The preparation is usually applied by hand by the user. In this regard, personal protective clothing is preferably worn, especially protective gloves, for example, made of plastic or latex (disposable gloves). However it is also possible to apply the preparation onto the keratinic fibers with an application aid. The application and contact time temperature for the preparation is from room temperature to 45° C. The action of the preparation can optionally be intensified by means of an external heat supply such as a heating hood. The preferred duration of treatment of the preparation on the keratinic fibers is 2 to 60 minutes, preferably 5 to 45 minutes. At the end of the treatment period, the remaining agent is washed out of the keratinic fibers with the help of a cleaning preparation or water. Once washed out, the keratinic fibers are optionally dried with a towel or with a hot air blower.

A further subject matter of the present invention is the cosmetic, non-therapeutic use of an agent of the first subject matter of the invention for improving the lightening power during the oxidative lightening or dyeing of keratinic fibers, especially human hair.

A further subject matter of the present invention is the cosmetic, non-therapeutic use of an agent of the first subject matter of the invention for improving the grey coverage during the oxidative dyeing of keratinic fibers, especially human hair.

Agents according to the invention can be produced from two or more separately packaged preparations immediately prior to use. This lends itself in particular to the separation of incompatible ingredients in order to avoid premature reaction.

A further subject matter of the present invention is a kit of parts containing:
- at least one first container (C1) with a preparation (A) comprising in a cosmetic carrier at least one alkanolamine according to Formula (I) and at least one alkanolamine according to Formula (II), and
- at least one second container (C2) with a developer preparation (B) comprising in a cosmetic carrier at least one oxidizing agent, wherein both preparation (A) as well as developer preparation (B) are free of ammonia.

The term "container" herein designates a holder which, regardless of its shape, material or closure, is capable of containing substances or mixtures of substances. Consequently, the term "container" includes, but is not limited to the interior of a tube, a pouch or bag, a canister, a can, a pan, a bottle, a glass or a packet, a carton, a box, an envelope or other containers. The components of a dyeing preparation can be present in a single container, although it is also possible and where appropriate, to separate them in various containers, and to instruct the consumer to mix them together before use.

A preferred embodiment of the subject matter of the invention is a kit of parts, wherein preparation (A) comprises at least one chromophoric component chosen from at least one oxidation dye precursor and/or at least one substantive dye.

In a particularly preferred embodiment, the packaging unit has at least one additional component chosen from personal protective clothing such as disposable gloves, apron; application aid such as comb, brush, paint brush or applicette; and instructions for use. The instructions for use comprise information and directions for the consumer for using the agent from the containers of the packaging unit in a process according to the first subject matter of the invention. An applicette is understood to mean a wide pencil whose shaft ends in a tip that facilitates and enables the fiber bundles or meshes to be divided from the totality of fibers.

The ready-for-use lightening and/or dyeing agent is produced by mixing preparation (A) with developer preparation (B) from the kit of parts.

Preferred embodiments of the first subject matter of the invention apply mutatis mutandis for the inventive use and packaging unit of the further subject matters of the invention. The following examples are intended to illustrate preferred embodiments of the invention without, however, limiting it.

EXAMPLES FOR LIGHTENING AND DYEING 1.1 Preparation of a Lightening Cream

Blonding creams were produced from the following listed ingredients:

| Raw material | Wt % | | | | |
|---|---|---|---|---|---|
| | E1 | V1 | V2 | V3 | V4 |
| Ammonium carbomer, 1.0% | — | — | — | — | 15.7 |
| Sodium lauryl ether sulfate | — | — | — | — | 0.74 |
| Potassium oleic soap, 12.5% | — | — | — | — | 3.15 |
| Lanette N | 14.00 | 14.00 | 14.00 | 14.00 | — |
| Xanthan | 0.05 | 0.05 | 0.05 | 0.05 | — |
| Cetiol V | 2.30 | 2.30 | 2.30 | 2.30 | — |
| Cetearyl alcohol | 3.90 | 3.90 | 3.90 | 3.90 | 12.60 |
| Cutina GMS SE | 6.00 | 6.00 | 6.00 | 6.00 | 2.10 |
| Cutina AGS | — | — | — | — | 2.10 |
| Eutanol G | — | — | — | — | 2.10 |
| Ceteareth-20 | — | — | — | — | 3.15 |
| Titanium dioxide | — | — | — | — | 0.50 |
| Merquat Plus 3330 | — | — | — | — | 1.50 |
| Phospholipid EFA | — | — | — | — | 0.10 |
| Cocosamidopropyl-betaine, 40% | 2.00 | 2.00 | 2.00 | 2.00 | — |
| Sodium sulfate | 0.30 | 0.30 | 0.30 | 0.30 | — |
| Ascorbic acid | 0.10 | 0.10 | 0.10 | 0.10 | 0.05 |
| Sodium silicate 40/42 | 0.50 | 0.50 | 0.50 | 0.50 | — |
| RonaCare Ectoin | 0.20 | 0.20 | 0.20 | 0.20 | — |
| RonaCare Tiliroside | 1.00 | 1.00 | 1.00 | 1.00 | — |
| Grape seed oil | 1.00 | 1.00 | 1.00 | 1.00 | — |
| EDTA, Na4, 87% | — | — | — | — | 0.20 |
| Monoethanolamine | 4.00 | 8.00 | 12.00 | — | — |
| 2-Amino-2-methyl-propanol | 4.00 | — | — | 8.00 | — |
| Ammonia, 25% | — | — | — | — | 10.00 |
| Perfume | qs | qs | qs | qs | qs |
| Water | ad 100 | ad 100 | ad 100 | ad 100 | ad 100 |

Lanette N INCI name: Cetearyl alcohol, Sodium Cetearyl Sulfate (Cognis)
Cetiol V INCI name: Decyl Oleate (Cognis)
Cutina GMS SE INCI name: Glyceryl Stearate (Cognis)
Cutina AGS INCI name: Glycol Distearate (Cognis)
Eutanol G INCI name: Octyldodecanol (Cognis)
Merquat Plus 3330 INCI name: Polyquaternium-39 (Nalco)
Phospholipid EFA INCI name: Linoleamidopropyl PG-Dimonium Chloride Phosphate (Uniquema)
RonaCare Eetion INCI name: Ectoin (Rona/Merck KGaA)
RonaCare Tiliroside INCI name: Sorbitol, Tiliroside (Rona/Merck KGaA)
Sodium silicate 40/42 sodium water glass The fats and surfactants were melted together at 80° C. and dispersed with part of the water. The remaining components of the formulation were then successively incorporated with stirring. Water was then added to make up 100 wt % and the formulation was stirred without heating.

Formulations V1 to V3 are non-inventive examples. Formulation E1 is an inventive example with the combination of the structurally different alkanolamines. V4 is a conventional, oxidative lightening agent with ammonia as the alkalizer.

1.2 Mixing with Developer Dispersions and Application

The lightening creams were mixed in a 1:1 ratio with a developer dispersion (figures in wt %) as follows—

| Raw material | EW1 | EW2 | EW3 | EW4 | EW5 |
|---|---|---|---|---|---|
| Potassium hydroxide, 50% | | | each 0.12 | | |
| Sodium benzoate | | | each 0.04 | | |
| Disodium pyrophosphate | | | each 0.10 | | |
| HEDP, 60% | | | each 0.25 | | |

-continued

| Raw material | EW1 | EW2 | EW3 | EW4 | EW5 |
|---|---|---|---|---|---|
| Isopropyl myristate | | each 0.80 | | | |
| Cetearyl alcohol | | each 4.00 | | | |
| Ceteareth-20 | | each 1.00 | | | |
| Beeswax | | each 0.30 | | | |
| Hydrogen peroxide, 50% | 5.1 | 11.1 | 17.0 | 23.0 | 24.0 |
| Water | | each ad 100 | | | |

For the application, strands of light brown hair (Fischbach-Miller) weighing approximately 0.7 g were treated with 4 times the amount of finished application mixture. After the strands had been treated for 45 minutes at 35° C. they were washed with a conventional shampoo and dried with a hair dryer.

1.3 Evaluation of Lightening Power

Colorimetric measurements were carried out on each of the strands at 4 measurement points. The measurement apparatus was the Spectralflash SF 450 from the Datacolor Company.

Measurement results were quantified with the help of the CIELAB color space.

The L-value represents the lightness of the dyeing (black-white axis); the greater the L-value, the lighter is the dyeing. The higher the L value, the stronger is the lightening of each nuance.

The following lightening results were obtained:

| Formulation | Developer-dispersion | pH | $H_2O_2$ content of application mixture [%] | ΔL |
|---|---|---|---|---|
| E1 | EW1 | 9.9 | 1.25 | 11.6 |
| E1 | EW2 | 9.9 | 2.75 | 14.4 |
| E1 | EW3 | 9.9 | 4.25 | 14.1 |
| E1 | EW4 | 9.9 | 5.75 | 16.3 |
| V1 | EW4 | 9.2 | 5.75 | 7.2 |
| V2 | EW4 | 9.9 | 5.75 | 15.9 |
| V3 | EW4 | 9.9 | 5.75 | 12.2 |
| V2 | EW5 | 10.0 | 6.00 | 19.9 |

Even with markedly lower hydrogen peroxide concentrations, the inventive lightening agents (E1) show a significant improvement in the lightening power (L value) in comparison with the relevant comparative formulations V1 and V3 without the inventive alkanolamine combination. Even agents with a markedly higher content of alkanolamine (V2) do not attain the lightening power of the inventive agent E1.

With E1, lightening values are nearly achieved that are otherwise only obtainable with ammonia-containing agents (V4).

2.1 Dyes

Each of the following dye mixtures was additionally incorporated into agents E1 and V1 according to 1.1: p-toluylenediamine sulfate (0.30 wt %); resorcinol (0.03 wt %); 2-methylresorcinol (0.07 wt %); 4-chlororesorcinol (0.04 wt %); 2-amino-3-hydroxypyridine (0.03 wt %); 2-amino-6-chloro-4-nitrophenol (0.02 wt %) and 2-(4-methyl-2-nitrophenyl) aminoethanol (0.02 wt %). This afforded the dyes E1* and V1*.

2.2 Coloration/Grey Covering

Developer preparation (EW4) was added to each agent according to section 2.1 and used in the half side test on test subjects' hair with medium to strong degrees of greyness for 45 minutes at 35° C. The hair was then rinsed out, dried with a hair drier and the coloration results were determined by skilled personnel.

It was found that the inventive agent E1* compared to V1* led to a markedly improved grey coverage.

We claim:

1. Agent for oxidatively dyeing and/or lightening keratinic fibers, comprising in a cosmetic carrier:
    at least one oxidizing agent chosen from hydrogen peroxide and/or its solid addition products on inorganic or organic compounds,
    at least one alkanolamine according to Formula (I),

$$NH_{3-x}(CH_2CH_2OH)_x \quad (I),$$

wherein x is 1, 2 or 3, and
    at least one alkanolamine according to Formula (II),

wherein R1 and R2 are independently hydrogen, a $C_1$-$C_6$ alkyl group or a $C_1$-$C_6$ hydroxyalkyl group, or R1 and R2 together with the carbon atom of the alkanolamine form a ring having 4 to 8 ring atoms and optionally having 1 to 2 hetero atoms, with the proviso that R1 and R2 are not simultaneously hydrogen,
    wherein the agent is free of ammonia.

2. Agent according to claim 1, wherein the at least one alkanolamine according to Formula (I) is at least monoethanolamine.

3. Agent according to claim 1, wherein the agent comprises as the at least one alkanolamine according to Formula (II) at least one compound according to Formula (II) wherein R1 and/or R2 is a $C_1$-$C_6$ alkyl group, or R1 and R2 together with the carbon atom of the alkanolamine is a cyclopentyl group, a cyclohexyl group or a tetrahydropyran group.

4. Agent according to claim 1, wherein the at least one alkanolamine according to Formula (I) is at least monoethanolamine, and wherein R1 and R2 in the at least one alkanolamine according to Formula (II) are each a methyl group.

5. Agent according to claim 1, wherein the alkanolamines according to Formula (I) and alkanolamines according to Formula (II) are present in a total amount of 0.5 to 25 wt %, based on total weight of the ready-for-use agent, wherein the weight ratio between alkanolamines according to Formula (I) and alkanolamines according to Formula (II) is from 1 to 10 to 10 to 1.

6. Agent according to claim 5, wherein the alkanolamines according to Formula (I) and alkanolamines according to Formula (II) are present in a total amount of 1 to 20 wt %, based on total weight of the ready-for-use agent, wherein the weight ratio between alkanolamines according to Formula (I) and alkanolamines according to Formula (II) is from 1 to 2 to 2 to 1.

7. Agent according to claim 1 further comprising at least one oxidation dye precursor and/or substantive dye as a color changing component.

8. Agent according to claim 1 further comprising at least one fatty component chosen from fatty acid alkyl esters of the formula $RCO_2R'$, wherein R is a $C_7$-$C_{21}$ alkyl group or $C_7$-$C_{21}$ alkenyl group and R' is a $C_8$-$C_{22}$ alkyl group or $C_8$-$C_{22}$ alkenyl group.

9. Method of improving the lightening power when oxidatively lightening or dyeing hair comprising applying an agent according to claim 1 to the hair for oxidative lightening or dyeing of keratinic fibers.

10. Method of improving the grey covering when oxidatively dyeing hair comprising applying an agent according to claim 1 to the hair for oxidative dyeing of keratinic fibers.

11. Kit of parts comprising:
at least one first container (C1) having a preparation (A) comprising in a cosmetic carrier at least one alkanolamine according to Formula (I)

wherein x is one of the numbers 1, 2 or 3, and
and at least one alkanolamine according to Formula (II),

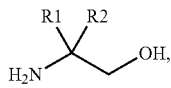

wherein R1 and R2 are independently hydrogen, a $C_1$-$C_6$ alkyl group or a $C_1$-$C_6$ hydroxyalkyl group or R1 and R2 together with the carbon atom of the alkanolamine form a ring having 4 to 8 ring atoms and optionally can comprise 1 to 2 hetero atoms, with the proviso that R1 and R2 are not simultaneously hydrogen, and at least one second container (C2) having a developer preparation (B) comprising in a cosmetic carrier at least one oxidizing agent, wherein both preparation (A) and developer preparation (B) are free of ammonia.

12. Kit of parts according to claim 11, wherein preparation (A) further comprises at least one chromophoric component chosen from at least one oxidation dye precursor and/or at least one substantive dye.

* * * * *